United States Patent [19]

Insana et al.

[11] Patent Number: 4,982,339
[45] Date of Patent: * Jan. 1, 1991

[54] HIGH SPEED TEXTURE DISCRIMINATOR FOR ULTRASONIC IMAGING

[75] Inventors: Michael F. Insana; Stephen W. Smith, both of Rockville; David G. Brown, Derwood; Robert F. Wagner, Gaithersburg, all of Md.

[73] Assignee: The United States of America as represented by Department of Health and Human Service, Washington, D.C.

[ * ] Notice: The portion of the term of this patent subsequent to Mar. 28, 2006 has been disclaimed.

[21] Appl. No.: 298,022

[22] Filed: Jan. 18, 1989

Related U.S. Application Data

[63] Continuation of Ser. No. 798,930, Nov. 18, 1985, Pat. No. 4,817,015.

[51] Int. Cl.$^5$ .................... A61B 10/00; G06F 15/20
[52] U.S. Cl. ............................ 364/507; 364/413.25; 128/660.01; 73/599; 73/602
[58] Field of Search ............... 364/550, 551.01, 554, 364/507, 413.25, 413.13, 413.14, 413.15, 413.22; 128/660.01; 73/599, 602, 606

[56] References Cited

U.S. PATENT DOCUMENTS

| | | | |
|---|---|---|---|
| 4,202,215 | 5/1980 | Meyer | 73/599 |
| 4,283,953 | 8/1981 | Plona | 73/589 |
| 4,327,588 | 5/1982 | North | 73/599 |
| 4,389,893 | 6/1983 | Cphir et al. | 73/599 |
| 4,412,544 | 11/1983 | Beretsky et al. | 128/660 |
| 4,441,368 | 4/1984 | Flax | 73/599 |
| 4,453,550 | 6/1984 | Flax | 128/660 |
| 4,475,396 | 10/1984 | Flax et al. | 73/599 |
| 4,475,398 | 10/1984 | Tjornehoj et al. | 73/599 |
| 4,512,195 | 4/1988 | Miwa et al. | 73/599 |
| 4,515,163 | 5/1985 | Flax et al. | 128/660 |
| 4,539,848 | 9/1985 | Takafuji et al. | 73/599 |
| 4,575,799 | 3/1986 | Miwa et al. | 364/413.25 |
| 4,747,411 | 5/1988 | Ledley | 364/413.25 |
| 4,752,896 | 6/1988 | Matsumoto | 364/413.25 |
| 4,817,016 | 3/1989 | Thompson et al. | 364/507 |
| 4,817,075 | 3/1989 | Insana et al. | 364/507 |

OTHER PUBLICATIONS

S. W. Flax, N. J. Pelc, G. H. Glover, F. D. Gutmann, M. McLachlan, Spectral Characterization and Attenuation Measurements in Ultrasound, Ultrasound Imaging, 5, 95–116, 1983.

L. L. Fellingham-Joynt, A Stochastic Approach to Ultrasonic Tissue Characterization, Standord Elect. Lab. Report G557-4, Jun. 1979.

D. J. Skorton, H. E. Melton, N. G. Panadian, J. Nichols, S. Koyanagi, M. L. Marcus, S. M. Collins, R. E. Kerber, Detection of Acute Myocardial Infarction in Closed Chest Dogs by Analysis of Two-Dimensional Echocardiographic Gray Level Distributions, Circ. Res. 52, 36, Jan. 1983.

R. Kuc, M. Schwartz and L. von Micsky, Parametic Estimation of the Acoustic Attenuation Coefficient Slope for Soft Tissue, IEEE Ultrasonics Symposium Proceedings, IEEE Ct. #76Ch 1120-5SU, 44–47, Mar. 1977.

(List continued on next page.)

Primary Examiner—Parshotam S. Lall
Assistant Examiner—Brian M. Mattson
Attorney, Agent, or Firm—Lowe, Price, LeBlanc, Becker & Shur

[57] ABSTRACT

Tissue signatures are obtained from first and second order statistics of an image texture to discriminate between different normal tissues and to detect abnormal conditions. These signatures described intrinsic backscatter properties of the tissue imaged and are used as the basis of an automatic tissue characterization algorithm. A device for on-line classifying of the texture of an image measures a total of four first and second order statistical properties of echo signals of a region of interest (ROI) selected by an operator, the echo signals being contained in an image memory. These can be used to obtain the tissue signatures, to detect low contrast lesions by machine, and to produce parametric images.

20 Claims, 5 Drawing Sheets

OTHER PUBLICATIONS

R. Kuc, Clinical Application of an Ultrasound Attentuation Coefficient Estimation Technique for Liver Pathology, IEEE Trans. Biomed. Eng. BME-27, Jan. 1980.

J. Ophir, R. E. McWhirt, N. F. Maklad, and P. M. Jaeger, A Narrow-Band Pulse-Echo Technique for in vivo Ultrasonic Attenuation Estimation, IEEE Trans. Biomed. Eng. BVE-32, 205–212, Mar. 1985.

S. Green, L. Joynt, P. J. Fitzgerald, D. Rubenson, R. L. Popp, In vivo Ultrasonic Tissue Characterization of Human Intracardiac Masses, Am. J. Cardiol. 51, 231, Jan. 1983.

Shimadzu, Ultrasonic Linear Array Scanner, Model SDL-150, 1985.

M. Matsumoto, T. Shimazu, M. Fujiwara, H. Nishioka, T. Matsuyama, K. Yasui, Y. Hamanaka, M. Inoue, H. Abe and H. Miwa, Ultrasonic Tissue Characterization of Infarcted Myocardium Employing Cepstral Analysis, WFUMB, 512, 1985.

F. G. Sommer, L. Fellingham-Joynt, B. A. Carroll, and A. Macovski, Ultrasonic Characterization of Abdominal Tissue via Digital Analysis of Backscattered Waveforms, Radiology, 141, 811–817, Dec. 1981.

L. L. Fellingham and F. G. Sommer, Ultrasonic Characterization of Tissue Structure in the in vivo Human Liver and Spleen, IEEE Trans. Sonics and Ultras. SU-31, 418–428, Jul. 1984.

D. L. King, F. L. Lizzi, E. J. Peleppa, P. M. Wai, M. M. Yaremko, M. C. Rorke, J. Herbst, Focal and Diffuse Liver Disease Studied by Quantitive Microstructural Sonography, Radiology, 155, 457–462, May 1985.

M. F. Insana, R. F. Wagner, B. S. Garra, D. G. Brown, and T. S. Shawker, Analysis of Ultrasound Image Texture via Generalized Rician Statistics, Proc. Soc. Photo-Opt Engrs., Aug. 1985.

J. W. Goodman, Statistical Properties of Laser Speckle Patterns, in Laser Speckle and Related Phenomena, J. C. Dainty, ed., 9–75, Berlin: Springer-Verlag, 1975.

R. F. Wagner, S. W. Smith, J. M. Sandrik, and H. Lopez, Statistics of Speckle in Ultrasound B-Scans, IEEE Trans. Sonics and Ultrason. SU-30, 156–163, May 1983.

F. J. Lizzi, M. Greenbaum, E. J. Feleppa, M. Elbaum, and D. J. Coleman, Theorectical Framework for Spectrum Analysis in Ultrasonic Tissue Characterization, J. Acoust. Soc. Amer., 73, 1366–1373, Apr. 1983.

U. Raeth, D. Schlaps, B. Limberg, I. Zung, A. Lorenz, G. von Kaick, W. J. Lorenz, B. Kommerell, Diagnostic Accuracy of Computerized B-Scan Texture Analysis and Conventional Ultrasonography in Diffuse Parenchymal and Malignant Liver Disease, J. Clin. Ultra. 13, 87–99, Feb. 1985.

R. W. Wagner, M. F. Insana, and D. G. Brown, Unified Approach to the Detection and Classification of Speckle Texture in Diagnostic Ultrasound, Proc. Soc. Photo-Opt. Engrs., Aug. 1985.

HIGH SPEED TEXTURE DISCRIMINATOR FOR ULTRASONIC IMAGING

This application is a continuation application of Ser. No. 798,930 filed Nov. 18, 1985, now U.S. Pat. No. 4,817,015.

FIELD OF INVENTION

The present invention relates to tissue characterization of ultrasound images, and, more particularly, to a high speed texture discriminator that measures first and second order statistical properties of echo signals.

BACKGROUND OF THE INVENTION

In many medical applications, ultrasonic imaging has provided a low cost and effective method of diagnosing disease. B-scan images are two-dimensional maps of acoustic echoes from tissue components. These images have a textured or speckled appearance that is characteristic of the interaction between the fairly coherent pulse transmitted and the scattering sites in tissues. Texture is often viewed as image noise which hinders the detection and interpretation of such signals of soft tissue lesions. However, with appropriate statistical analysis, quantitative information specific to imaging performance and tissue characteristics can be extracted from the image texture Detecting the presence of disease in tissue parenchyma on a quantitative, operator independent basis is the objective of tissue characterization methods. Toward this goal, many ultrasonic tissue characterization techniques have been proposed. The success of these methods depends, however, on how well measured acoustic properties or signal parameters correlate with disease states. The most widely studied characterization method is measurement of ultrasonic attenuation, which represents the total lineal loss of acoustic energy for ultrasound propagating through tissue. A number of spectral and time domain techniques have been proposed. Two attenuation techniques have been implemented in prototype commercial clinical B-scanning hardware.

Several patents, such as U.S. Pat. Nos. 4,475,397 and 4,515,163, have disclosed devices for determining the attenuation coefficient of tissue from zero crossings to frequency spectrum of reflected waves. Others like Miwa in U.S. Pat. No. 4,509,524 determine the attenuation coefficient of the tissue by comparing reflected waves of different frequencies with a reference medium. The Flax et al. U.S. Pat. No. 4,475,396 discloses a time-based method of determining attenuation coefficient.

Stochastic methods for analyzing image texture have become a topic of increasing scientific interest because the results can be directly related to observable image characteristics and physical scattering properties. Several research groups have conducted off-line studies of the moments of first order statistics such as mean, variance and kurtosis as measures of tissue characterization. A common limitation of these studies is that the analysis is performed off-line with long turn-around times, diminishing effectiveness in any proposed clinical environment application.

Fellingham and Sommer (Ultrasonic Characterization of Tissue Structure in the In Vivo Liver and Spleen, IEEE Transactions on Sonics and Ultrasonics, Vol. SU-31, No. 4, July 1984) describe measurement of mean scatterer spacing as a tool for tissue characterization.

In all the above systems, there is either insufficient information for tissue characterization and discrimination, or there is not present a strong physical-statistical basis for the analysis of tissue images, specifically for discrimination in low contrast media.

Thus, in spite of the great need which has existed for many years, and the very great activity among researchers and practical workers in the art, there has not previously been provided a satisfactory system for rapidly detecting on-line the presence of disease in tissue parenchyma on a quantitative, operator independent basis, using ultrasonic imaging.

SUMMARY OF THE INVENTION

Accordingly, it is an object of the present invention to overcome deficiencies in the prior art, such as indicated above.

It is another object of the invention to provide improved ultrasonic imaging information.

It is a further object to detect the presence of disease in tissue parenchyma on a quantitative, operator independent basis.

It is yet another object to provide an improved method of tissue characterization that uses, in addition to the mean spacing of periodic tissue scatterers, intrinsic backscatter properties of tissues which can be estimated from the image statistics.

Still another object of the present invention is to provide a device for high speed on-line implementation of the above method which is adaptable to currently in-use ultrasound imaging devices.

A further object of the present invention is to provide a device for detecting low contrast lesions, and another object is to provide a device for producing parametric images.

BRIEF DESCRIPTION OF THE DRAWINGS

Other objects and the nature and advantages of the instant invention will be more apparent from the following detailed description of the invention taken in conjunction with the drawing, wherein.

DETAILED DESCRIPTION OF EMBODIMENTS

Studies over the years have shown that tissue scatterers vary in size and shape, and that different biological structures have varying degrees of spatial order. The simplest biological scattering medium is unclotted blood which is completely disordered, consisting of randomly distributed Rayleigh scatterers. At the other extreme is the very complex anisotropic structure of skeletal muscle tissue. This tissue is highly ordered, with nearly periodic scatterers that repeat over a long range.

The organization of scattering structures for most media falls somewhere in between blood and skeletal muscle, and it is for these structures that the problem of detecting such organized structure by means of ultrasonic imaging has been so difficult.

Backscatter properties can be derived from the intensity image $I(z,\theta)$, which is defined as the squared envelope of the complex ultrasonic echo signal $g(z,\theta)$, or $I=|g|^2$. Here z is the range direction and $\theta$ is the sector angle in a sector B-scan image or the scan direction in a rectangular format. The echo signal $g(z,\theta)$ is the sum of scattering from a diffuse (incoherent) component, $g_r + ig_i$, and a specular (coherent) component $R(z,\theta)$ from scattering sites with semi-periodic, long range order, a function of position. The average intensity autocorrelation function, $R_I(\Delta z)$ for a region of interest (ROI) in the intensity image is calculated along the range direction, i.e. along the z direction. The ROI is chosen so that the effect of specular scatterers such as blood vessels and organ surfaces can be assumed to be negligible.

We have now derived the expression for $R_I(\Delta z)$ assuming a Rician probability distribution function (pdf):

$$R_I(\Delta z) = <I(z_1)I(z_2)> = I_d^2(1+|\rho|^2) + 2I_d I_s + <I_s(z_1)^* I_s(z_2)> + 2 I_d \rho <R(z_1)^* R(z_2)> \quad (1)$$

$I_d$ = diffuse or average incoherent backscatter intensity, $\bar{I}_s$ is the average specular backscatter intensity, $\bar{I}=I_d+\bar{I}_s$, and $\rho$ is the complex coherence factor. For stationary data, the last two terms can be interpreted as average autocorrelations of $I_s$ and $\bar{R}$ averaged over $\theta$.

To form the features space, in the present invention the following three values of $R_I(\Delta z)$ at the lags $\Delta z$ are defined, recognizing that the mean square $I^2$ and squared mean $(\bar{I})^2$ may be obtained by setting $\rho = 1$ and $\rho = 0$, respectively, in Eq. 1.

$$t = R_I(0) = 2I_d^2 + 4I_d I_s = \bar{I}_s^2 \quad (2)$$

$$p = R_I(\bar{d}) = I_d^2 + 2I_d I_s + I_s^2 \quad (3)$$

$$b = R_I(\Delta z >> \bar{d}) = (I_d + I_s)^2 \quad (4)$$

Figure 1:
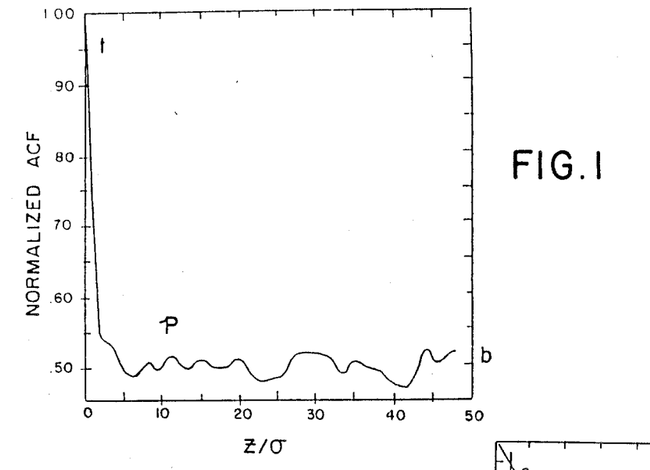
FIG. 1 is a graph which shows the average autocorrelation function in the range direction, specifying t, p, and b, three parameters of texture discrimination.

There is also a fourth parameter $\bar{d}$, the average spacing between resolvable specular scatterers, which may be found from the lag value separating correlation peaks in $R_I(\Delta z)$ (FIG. 1). It is however, more easily measured from peaks in the power spectrum.

Through simple quadratic relations, the parameters t, p, and b are related to the scattering properties of the imaged tissues.

$$I_d = (b)^{\frac{1}{2}} - (b-t+p)^{\frac{1}{2}} \quad (5)$$

$$I_s = (b-t=p)^{\frac{1}{2}} \quad (6)$$

$$\text{var}^{\frac{1}{2}}(I_s) = (p-b)^{\frac{1}{2}} \quad (7)$$

Here t is the second moment of the intensity image and b is the square of the first moment. Thus, the parameter b is the squared mean of the intensity image, a measure of mean ultrasound backscatter intensity in the ROI. The parameter t−b is the variance in the intensity image from both random and specular scatterers, i.e. the Rician noise variance. If the tissue contains no specular scatterers or if the spacing between the specular scatterers is closer than the resolution of the imaging system, then only the two first order parameters t and b are relevant; i.e., p=b and $\bar{d}$ cannot be measured. There are, however, tissues which contain a semi-periodic array of specular scatterers at some spacing $\bar{d}$ resolvable by the ultrasonic imaging device but not detectable in the image by the human observer due to the image texture noise.

Figure 2:
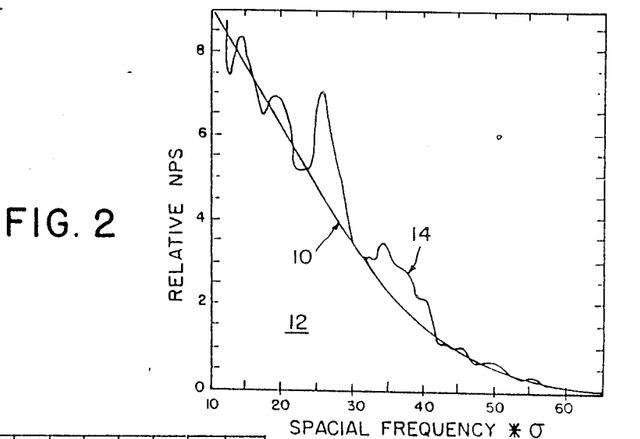
FIG. 2 is a graph which illustrates the average power spectrum, and in which the area 12 below the curve 10 indicates the Rician noise contribution to the image variance, and d a fourth texture parameter is specified by the inverse of the spatial frequency of peaks 14 in the power spectrum.

It is difficult to measure the height p (peak) in $R_I(\bar{d})$ because, for most soft tissues, the correlation peaks are small compared to the uncertainty of the measurement and often there is more than one set of semi-periodic structures. A better estimate of p involves partitioning the power spectrum estimate, $W(f)$ (FIG. 2).

$$W(f) = \delta(f)(I_d + I_s)^2 + I_d^2 P^* P + <\Delta I_s^2(f)> + 2I_d PR^{2-} + 2I_d P^* <\Delta R^2(f)>, \quad (8)$$

where $\rho$ and P, R and R, and $I_s$ and $I_s$ are Fourier transform pairs, and $\delta$ indicates as usual the Dirac delta function of its argument.

Figure 3:
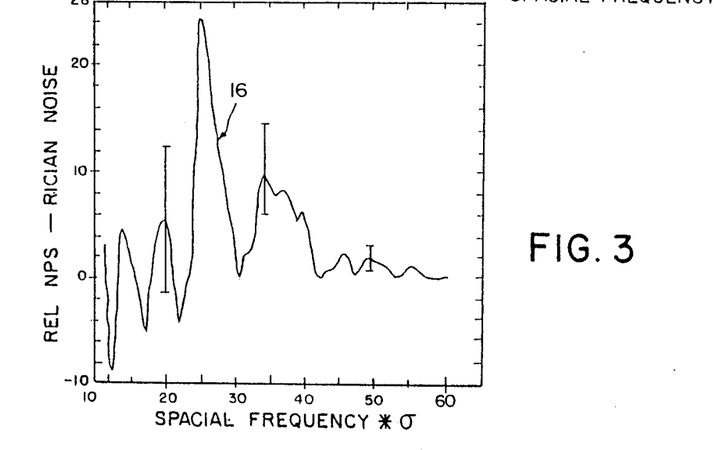
FIG. 3 is a graph 16 showing the power spectrum with Rician noise subtracted and in which error bars denote ± one standard deviation.

Furthermore, we have written $I_s(f)$ as $$\delta(f)I_s + \Delta I_s(f'),$$

where f' means for all f other than f=0. We can show that for line spectra, the variance in the specular intensity, the integral of the third term in Eq. 8 over for can be separated from the rest of the spectrum. In practice, this is done by fitting the spectral minima to a Gaussian function 10, as shown in FIG. 2. The Gaussian function is chosen because the incident pulse has a Gaussian spectrum and because data is processed only along the beam axis. The Rician noise 12, the area below the fitted line 10, is then subtracted from the original spectrum 14, and the result integrated (FIG. 3) to obtain the difference quantity p−b.

The scattering quantities t, p, b, and $\bar{d}$ form a four-dimensional feature space that is sensitive to changes in tissue microstructure which may result from disease processes and may, therefore, provide diagnostically significant tissue signatures. The analysis has been shown to accurately discriminate among subtle changes in texture that are not easily detected by the human observer.

The structure of a preferred embodiment of a texture discriminator (TD) according to the invention and its application in an ultrasound B-scanner is discussed in detail below in accordance with FIGS. 4–7.

Figure 4:
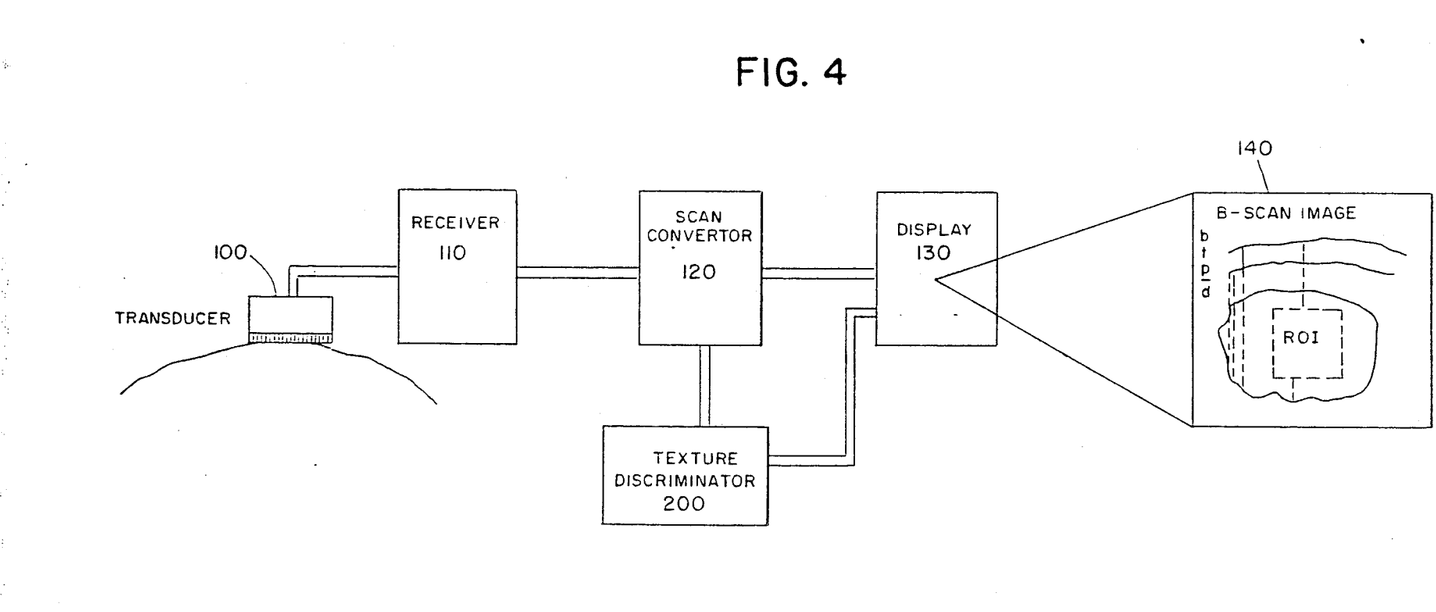
FIG. 4 is a schematic block diagram of a common ultrasound imaging device equipped with a texture discriminator according to the invention.

FIG. 4 shows a block diagram of a typical ultrasonic B-scanner, in this case a conventional sequential linear array system. The scanner includes a transducer 100, receiver circuitry 110 including any delay line and video processing, a scan convertor 120, the subject texture discriminator 200, and a display monitor 130. The insert 140 for the display monitor illustrates a cross-sectional B-scan in normal rectangular format consisting of many B-mode lines. The image also includes a region of interest as shown by the dashed rectangle.

The letters p, t, b and $\bar{d}$ in the upper left corner of the image illustrate the numerical display of the tissue signature variables obtained by the texture discriminator to be described below. Analogous block diagrams would apply for all other clinical ultrasonic B-scan devices including mechanical sector scanners, phased array sector scanners and static compound B-scanners.

In a typical embodiment of the invention, the texture discriminator operates on digital pixel data contained in a region of interest of the conventional B-mode scan convertor. In this preferred embodiment, the ROI consists of an N=64 pixel by M=64 pixel area of eight bit image data chosen by the operator from a 512×512 field of view. The image pixel data in the ROI, thus isolated from the original pixel data, is available for transfer to the texture discriminator. The ROI selection is a common feature of commercial ultrasound imaging devices used for length and area calculations, magnification views and prototype attenuation tissue signature measurements. In this embodiment one complete operation of the texture discriminator is carried out in less than 90 msec. Thus, display of the tissue signature parameter is updated at a rate of approximately, once every three video frames.

The echo signals in the ROI have been processed by the same conventional envelope detection as the B-scan image. The first step of the TD is to square the 2-dimensional array of echo envelope data $x_{ij}$ in the ROI to form a corresponding intensity image of values $I_{ij}=x_{ij}^2$. This is followed by calculation of two first order image statistics b and t, $$\text{where } b = \left[ \sum_{i=1}^{M} \sum_{j=1}^{N} I_{ij} \right]^2 / (MN)^2 \quad (9)$$

$$\text{and } t = \sum_{i=1}^{M} \sum_{j=1}^{N} (I_{ij})^2 / (MN). \quad (10)$$

To characterize tissues with texture having generalized Rician character, the TD, in parallel with the measurement of b and t, also determines two second order texture statistics from the ultrasound intensity image. These are $\bar{d}$ and p which are obtained from the average noise power spectrum (NPS). FIG. 2 shows an average NPS 14 from a B-scan of normal human liver obtained by averaging, in the lateral direction, 64 one-dimensional NPSs measured from data along the axial direction of a 64×64 ROI.

The average NPS 14 shows several peaks at identifiable spatial frequencies from which the tissue scatterer average spacing $\bar{d}$ is obtained. The other second order statistical parameter measured by the texture discriminator is p, the variance of ultrasonic backscatter intensity due to the ordered tissue structure discussed above. p−b is obtained from the NPS by numerically separating the Rician noise 10 contribution to the NPS 14 from the variance in the specular intensity. Curve 10 illustrates the Rician noise component which is removed, so that a resulting summation of the net NPS 16 (FIG. 3) yields the described parameter p - b.

The four parameters t, p, b, and $\bar{d}$ uniquely specify the acoustic characteristics of the tissue in the defined ROI for medical diagnosis. The details of the on-line measurement of these variables in the texture discriminator will now be described.

Figure 6:
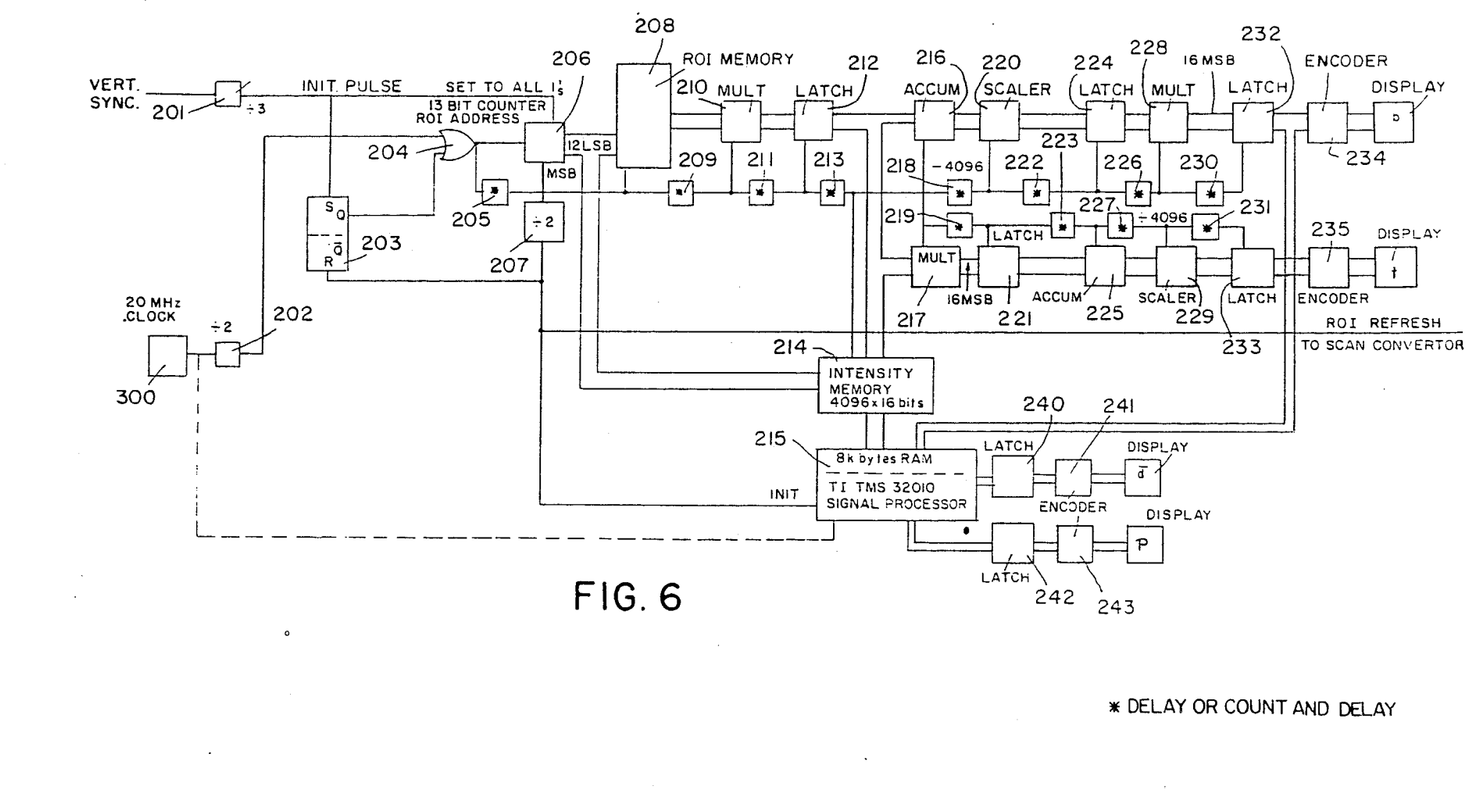
FIG. 6 is a schematic block diagram of a preferred embodiment of the present invention.

The operation of the texture discriminator (TD) 200 of FIG. 4 in determining b is illustrated further in FIG. 6. The flowchart 400 which shows the b measurement includes tee squaring of the pixel data, x(m), the accumulated sum of the intensities, and the final scaling and squaring to obtain b.

Figure 5:
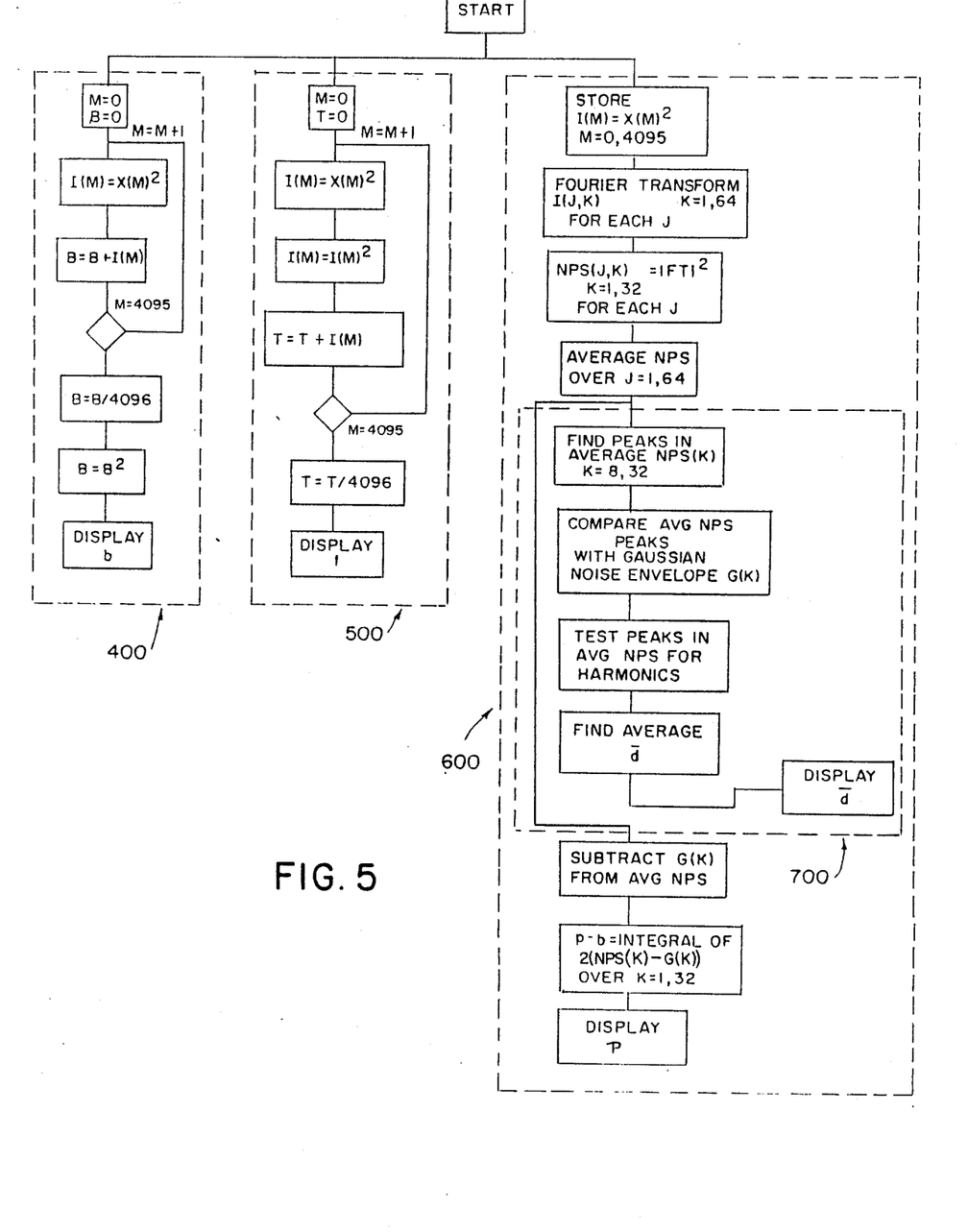
FIG. 5 is a three section flowchart outlining the process of obtaining first and second order statistics of the scanned region of interest ROI.

The flowchart 500 of FIG. 5 shows the t measurement; which includes raising the pixel data x(m) to the fourth power $I^2(m)$, the summing operation, and the final averaging to obtain t. Similarly higher moments of the first order statistics, such as variance or kurtosis, can be determined and displayed by analogous high speed digital operations.

FIG. 6 is a schematic of the texture discriminator (TD). In this preferred embodiment, the ROI feature of a conventional ultrasound scanner is assumed to operate continually so that the image pixel data within the ROI is stored in its own ROI memory 208 and is updated by conventional means every three video frames or 10 updates/second for a conventional 30 frame/per second real time ultrasound imaging device. The TD is initiated with the reception of a vertical sync pulse from the TV sync generator which is used to synchronize conventional scanners. The vertical sync pulse passes through a÷3 counter 201 so that the TD is initialized 10 times per second. The Init pulse sets the 13 bit ROI address counter 206 to all 1's. The Init pulse also sets flip-flop 203 whose Q output is one input to And gate 204.

The operation of the TD is paced by a 20 MHz master clock 300 resulting in a pulse rate of one pulse per 50 nsec. The output of the master clock 300 passes through the ÷2 counter 202 and then forms the other input to And gate 204. Thus after the Init pulse, the output of And gate 204 increments the 13 bit ROI address counter 206 every 100 nsec. The most significant bit (MSB) of the counter 206 passes to the ÷2 counter 207.

The 13 bit ROI address counter 206 is incremented every 100 nsec. The 12 least significant bits of the address counter 206 determine the memory address of the 4096×8 bit ROI memory 208 which contains the ultrasound pixel data for the 64×64 ROI. The counter 206 also determines the address for the 4096×16 bit intensity memory 214. The ROI memory 208 is also cycled by the output of And 204 after a delay 205. Each eight bit pixel is then transferred in turn to both inputs of multiplier 210 to obtain the square of the pixel data, multiplier 210 in turn is cycled after the delay 209, and the 16 bits of the pixel intensity word is transferred to latch 212.

Latch 212 is cycled after delay 211, and the pixel intensity word is transferred to three destinations simultaneously: accumulator 216, multiplier 217 and the correct address of the intensity memory 214. The intensity data is summed in accumulator 216 with each count of the 12 bit ROI address counter 206 as delayed by delay 213. When the counter 218 reaches 4095, the accumulated sum is passed to scaler 220 which forms a mean value of the backscattered ultrasound intensity and then to latch 224 after delay 222. The data is then sent to multiplier 228 after a delay 226 to form the mean intensity squared. Finally, this value is sent to latch 232 after a delay 230 and then to the digital encoder 234 for display. The b value is also sent to the signal processor 215 for later use.

In the parallel operation for the t parameter, the output of latch 212 passes to multiplier 217, after delay 213, to form the square of each intensity pixel. This data passes to latch 221 after delay 219 and then to accumulator 225 after delay 223 to form the sum. When the address counter 227 or delay reaches 4095 the sum is passed to scaler 229 to form a mean and then to latch 233 after delay 231 and then to encoder 235 to form the t display.

In the third parallel operation, the pixel intensity data from latch 212 is loaded into the intensity memory 214, which is cycled after delay 213. These three parallel operations consume 409.6 μsec so that the b and t parameters are displayed at that time.

When the counter 206 reaches the count of 4096, at which point all the pixels are retrieved, the most significant bit (MSB) of the counter 206 passes to the ÷2 counter 207. The output of the ÷2 counter 207 resets flip-flop 203 so that its Q output is "low", disabling And gate 204 and thus holding the b and t values. The output of the ÷2 counter 207 also is sent to the signal processor 215 initiating the signal processor 215 operations, explained below, to determine the $\bar{d}$ and p parameters. The final value of the d parameter measured in signal processor 215 is transferred to latch 240 and then to digital encoder 241 for the display. The parameter p, which is also measured in signal processor 215, is passed to the latch 242 and then to encoder 243 for display.

Figure 7:
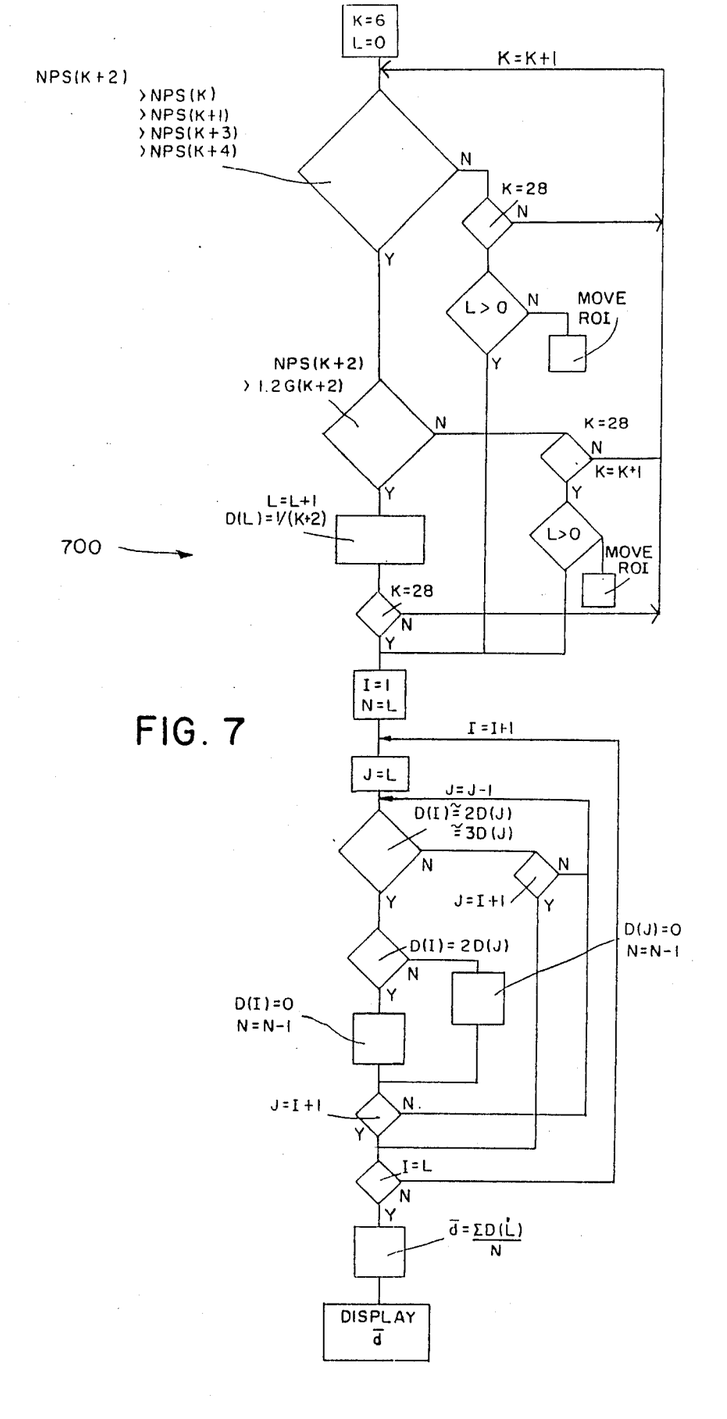
FIG. 7 is detailed flowchart of a process of measuring second order statistics of a texture discriminator of the present invention as shown in block 700 of FIG. 5.

Referring to FIGS. 5–7, the operation of signal processor 215 is explained in detail. The output of the ÷2 counter 207 initiates a Fourier transform (FT) operation in signal processor 215. The FT pulse is also passed to the scan converter 120 of FIG. 4 to initiate updating of the ROI memory 208 for the next video frame. A 64 sample FT is performed in the axial direction for each of the 64 intensity lines in the intensity memory 214 corresponding to the 64 B-mode lines in ROI. The initial 64 pixel intensity line is read from the intensity memory 214 into the random access memory (RAM) of the signal processor 215. The resulting complex FT is squared to obtain a 32 sample NPS and then stored in the RAM for subsequent averaging. The 64 FT's are performed sequentially, the resulting NPS's are accumulated in memory and then scaled to obtain an average NPS in the axial direction of the ROI. The elapsed time to perform these operations is approximately 41 msec.

Following the determination of the average NPS of the image ROI, additional signal processing functions are performed to obtain the parameters $\bar{d}$ and p as shown in FIG. 5 in the flow path 600 and in FIG. 7. By conversion of the algorithm to assembly language, this additional, non-FT signal processing will consume approximately 46 msec per ROI. The 32 sample average NPS is scanned to find the location of any local peaks as shown in the example average NPS of FIG. 2. The height of each detected peak in the average NPS is then compared to a Gaussian noise function $G(K)$, $K=1, 32$ stored in a look-up table in the memory of the signal processor 215 illustrated by the curve 10 in FIG. 2. The Gaussian noise function is precalculated based on conventional speckle size theory and the impulse response of the ultrasound transducer. If a detected peak in the NPS exceeds 120% of the Gaussian noise function, the sample location of the peak ($K=8, 32$) is stored. Next, the spatial frequency location of each unique NPS peak is converted to a spatial length via a look-up table contained in memory, which includes a scaled inverse of the samples $K=8, 32$. The sample locations of each peak are then tested for redundancy, i.e. the presence of harmonics or subharmonics. The locations of only unique peaks are averaged to obtain the average interscatterer spacing $\bar{d}$.

Subsequently, the Gaussian noise envelope $G(K)$ is subtracted from the average $NPS(K)$. The net values of the difference function are accumulated forming an equivalent integral of the area under the tissue structure peaks. The b value from latch 232 is then added to this integral, the sum being then scaled to form the parameter p.

An alternative method for determining the noise envelope, which need not depend on the pre-calculated spectral characteristics of the individual transducer, is to fit a Gaussian function to the minima of the average NPS. The function is then subtracted from NPS to determine p.

In this preferred embodiment of texture discriminator, it is assumed that the original 512×512 pixel image is obtained over a maximum range of 20 cm and is digitized in the scan convertor so that a 64×64 ROI results in a sample of approximately 25 mm×25 mm. Thus, a 64 sample FT yields an NPS of 32 unique values and a spatial frequency resolution of 0.04 mm$^1$. This yields a useful range to search for average tissue scatterer spacing of 0.8 to 3.1 mm, which lies within the axial resolution limits of a conventional 3.5 MHz abdominal or cardiac transducer.

In one embodiment, the Fourier transform is carried out using the commercially available Texas Instrument TMS32010/20 digital signal processor (including 8 kB of external memory for the TMS32010 and 256 kB for the TMS32020) which obtains a 64 sample FT in 0.63 msec. The TMS32010/20 uses a 20 MHz clock which is synchronized with the master clock.

The peak detection routine is limited from sample 8 to 32 to adhere to the spatial frequency limitation described above.

The total elapsed time for measurement of t, p, b and $\bar{d}$ is less than 90 msec. With the reception of the next television vertical sync pulse, from the ÷3 counter 201, flip-flop 203 is set again, and the texture discriminator is reset for operation.

In certain alternative embodiments, the texture discriminator includes measurement of the second order statistical parameters in the lateral direction. Furthermore, measurements can be made of higher order statistics using analogous designs. Also, second order statistical measurements can be obtained from the autocorrelation function (ACF), the Fourier transform of the NPS.

Furthermore, implementation of high speed on-line matched filters can be included to eliminate non-Gaussian interference, such as that due to blood vessels. Analogous hardware and standard algorithms can be used to implement, on-line and at high speed, other texture analyses such as cepstra and pattern recognition techniques, such as the co-occurrence matrix. Finally, analogous hardware and standard algorithms can be used to process the radio-frequency echo signals or the B-mode echo envelope signals instead of the intensity echo signal as described above. In each of these alternatives, multiple signal processing paths can be performed in parallel to increase speed.

Another feature of the TD is to store the ROI pixel data using the freeze frame option of the imaging device and then determine the tissue signature parameter at a slower rate. The advantage of this freeze frame implementation is that only data within a given frame is analyzed. This allows analysis of cardiac muscle, for example, that would normally be moving in and out of an ROI in real time. Of course, other various sizes and shapes of the ROI can also be used with corresponding longer or shorter operation times of the TD for any given examination.

The foregoing description of the principle and the specific embodiments will so fully reveal the general nature of the invention that others can, by applying current and disclosed knowledge, readily modify and/or adapt the disclosed embodiments for various implementation and/or other pertinent applications without departing from the generic concept. Therefore, such adaptations and modifications should and are intended to be comprehended within the meaning and scope of the disclosed embodiments.

It is also possible to carry out the invention by measuring other second order parameters, on-line and at high speed, such as cepstra and pattern recognition variables, e.g. run length statistics, co-occurrence matrices, "entropy".

What is claimed is:

1. A method of characterizing a region of interest in a body under examination, said region of interest including at least one of a semi-periodic structure and a periodic structure, said method comprising:
    providing a plurality of data for a corresponding plurality of volumeric parts of said region of interest, each said data corresponding to scattering of incident energy from the respective volumeric part, a number of said volumeric parts being located along at last one line defined thereby to extend in said region of interest through said at least semi-periodic structure, wherein said incident energy number of said volumeric parts and their location along said at least one line are such as to result in said data including information of a plurality of periods of said at least semi-periodic structure,
    calculating from said data at least (1) the value of a parameter p or (2) the values of at least two parameters selected from b, t, and $\bar{d}$, and
    classifying said region of interest of said body under examination based on at least one respective number derived from at least one of each said calculated value,
    wherein b indicates a squared mean of an intensity of said incident energy as scattered by said volumeric parts, t indicated a total variance in said intensity plus b, p indicates a variance in said intensity due only to at least one of said periodic and semi-periodic structure plus b, and d is an average distance characterizing said at least semi-periodic structure along said at least one line in said region of interest.

2. The method of claim 1, said calculating comprising calculating said value of b, t and p.

3. The method of claim 2, comprising calculating a numerical value of at least one of the parameters $I_d$, $I_s$ and $var^{\frac{1}{2}}(I_s)$, wherein $$I_d = b^{\frac{1}{2}} - (b - t + p)^{\frac{1}{2}},$$

$$I_s = (b - t + p)^{\frac{1}{2}}, \text{ and}$$

$$var^{\frac{1}{2}}(I_s) = (p - b)^{\frac{1}{2}}.$$

4. The method of claim 2, comprising the further step of calculating the values of a plurality of further parameters which are respective functions of said parameters b, t and p, said values of said further parameters being used for said classifying based on said at least one respective number.

5. The method of claim 1, comprising calculating numerical values of all four of said parameters, for said classifying of said region of interest.

6. The method of claim 1, comprising:
    calculating a value for at least one of said parameters for a plurality of regions of interest in said body under examination, using further respectively provided data for respective further ones of said volumeric parts, and
    associating each of said calculated value of said at least one parameter with the respective location in said body of the respective region of interest,
    wherein at least one respective parametric representation of said body under examination over said regions of interest is provided, each based on said calculated values of the respective parameter.

7. The method of claim 1, said incident energy propagating, prior to said scattering, along a direction of incidence, and said at least one line defined by said volumetric parts being a straight line parallel to said direction of incidence.

8. The method of claim 1, said incident energy propagating, prior to said scattering, along a direction of incidence, and said at least one line defined by said volumetric parts being a straight line perpendicular to said direction of incidence.

9. The method of claim 1, comprising calculating said value of said parameter b, and calculating the value of said parameter p by forming a noise power spectrum of said data for said volumetric parts along said at least one line, subtracting a Gaussian function from said noise power spectrum, integrating a remainder, and equating a value of the integrated remainder to b−p.

10. The method of claim 9, comprising calculating said Gaussian function for said subtracting based on speckle size theory and impulse response.

11. The method of claim 9, comprising determining said Gaussian function for said subtracting by fitting it to minima of a conjugate of a Fourier transform.

12. The method of claim 9, comprising forming said noise power spectrum as an average of a plurality thereof, each for a respective plurality of said data that are provided for a respective plurality of said volumetric parts each defining a respective one of said lines in said region of interest.

13. The method of claim 1, comprising forming said noise power spectrum by Fourier transforming said data for said volumetric parts along said at least one line.

14. The method of claim 1, comprising forming said noise power spectrum by forming an autocorrelation function of said data for said volumeric parts along said at least one line, and Fourier transforming said autocorrelation function.

15. The method of claim 1, comprising
    providing pluralities of said data for respective pluralities of said volumeric parts of said region of interest, wherein
    said pluralities of volumetric parts define a plurality of lines in said region of interest, all of said lines being parallel to each other, and
    all of said data are used for said calculating.

16. The method of claim 1, comprising calculating said parameter $\bar{d}$ by forming a noise power spectrum of said data for said volumeric parts along said at least one line, determining abscissa values at which peaks in said noise power spectrum occur, taking inverses of said abscissa values, eliminating redundancies from said inverses corresponding to harmonics and subharmonics of a period of said semi-periodic structure, and forming said parameter $\bar{d}$ as an average of reciprocals of remaining inverses.

17. A device for characterizing a region of interest in a body under examination, said region of interest including at least one of a semi-periodic structure, and a periodic structure, said device comprising:

means for providing a plurality of data for a corresponding plurality of volumetric parts of said region of interest, each said data corresponding to incident energy from the respective volumeric part, a number of said volumeric parts being located along at least one line defined thereby to extend in said region of interest through said at least semi-periodic structure, wherein said incident energy and the number of said volumetric parts and their location along said line are such as to result in said data including information of a plurality of periods of said at least semi-periodic structure, and means for calculating from said data at least (1) a value of a parameter p or (2) values of at least two parameters selected from b, t, and $\bar{d}$, and providing each calculated value for allowing classifying said region of interest of said body under examination based on each said calculated value, wherein b indicates a squared mean of an intensity of said incident energy as scattered by said volumeric parts, t indicates a total variance in said intensity plus b, p indicates a variance in said intensity due only to at least one of said periodic and semi-periodic structure plus b, and d is an average distance characterizing said at least semi-periodic structure along said at least one line in said region of interest.

18. The devices of claim 7, further comprising
means for providing a layer plurality of said data for a respective larger plurality of volumetric parts in said body under examination, and display means for displaying said larger plurality of data in association with a location of each respective volumetric part, wherein said region of interest for said calculating of each respective parameter value is selectively provided from the display.

19. The device of claim 18, wherein said display means provides a parametric image of said body under examination, based on respective calculated values of at least one of said parameters for a respective plurality of said regions of interest.

20. A device for determining an existence of at least one semi-periodic structure in a region of interest in a body under examination, comprising:

means for selecting said region of interest within said body under examination, means for providing data characteristic at least a magnitude of envelopes of scattering of incident energy from a plurality of volumeric parts in said region of interest, said incident energy and said plurality of volumeric parts being selected to contain information on a plurality of periods of said at least semi-periodic structure as a result of different envelope magnitudes for said scattering of said incident energy with a respective phase of said at least semi-period structure, and means for analyzing said data and for providing output for characterizing said region of interest based on said scattering of a plurality of periods of said at least semi-periodic structure, said output characterizing at least in part one of:

(1) a variance in said scattering from said plurality of volumeric parts due to said semi-periodic structure as sampled by said plurality of volumeric parts in said region of interest; and (2) both (i) a mean periodicity of said at least semi-periodic structure (ii) at least one of a mean scattering from all structure and a variance in said total scattering, as sampled by said plurality of volumeric parts in said region of interest.

* * * * *